(12) United States Patent
Le Floch

(10) Patent No.: US 9,116,119 B2
(45) Date of Patent: Aug. 25, 2015

(54) BRILLOUIN OPTOELECTRONIC MEASUREMENT METHOD AND APPARATUS

(75) Inventor: Sébastien Le Floch, Le Villeret (CH)

(73) Assignee: OMNISENS SA, Morges (CH)

( * ) Notice: Subject to any disclaimer, the term of this patent is extended or adjusted under 35 U.S.C. 154(b) by 103 days.

(21) Appl. No.: 13/991,249

(22) PCT Filed: Dec. 22, 2010

(86) PCT No.: PCT/EP2010/070585
§ 371 (c)(1),
(2), (4) Date: Jun. 3, 2013

(87) PCT Pub. No.: WO2012/084040
PCT Pub. Date: Jun. 28, 2012

(65) Prior Publication Data
US 2013/0265569 A1      Oct. 10, 2013

(51) Int. Cl.
*G01N 21/00* (2006.01)
*G01N 21/47* (2006.01)
*G01D 5/353* (2006.01)
*G01L 1/24* (2006.01)

(52) U.S. Cl.
CPC ............ *G01N 21/47* (2013.01); *G01D 5/35364* (2013.01); *G01L 1/242* (2013.01)

(58) Field of Classification Search
CPC ......... G01D 5/353; G01N 21/47; G01L 1/242
See application file for complete search history.

(56) References Cited

U.S. PATENT DOCUMENTS

| | | | | |
|---|---|---|---|---|
| 5,835,030 A * | 11/1998 | Tsutsui et al. | ................... | 341/51 |
| 6,459,479 B1 * | 10/2002 | Lee et al. | ................... | 356/73.1 |
| 6,917,668 B2 * | 7/2005 | Griffith | ................... | 378/163 |
| 7,414,754 B2 * | 8/2008 | Yamazoe | ................... | 358/1.9 |
| 2003/0035162 A1 * | 2/2003 | Myers et al. | ................... | 359/110 |
| 2010/0014071 A1 | 1/2010 | Hartog | | |

FOREIGN PATENT DOCUMENTS

| | | | | |
|---|---|---|---|---|
| CN | 101852627 A * | 10/2010 | ............... | G01D 5/36 |
| EP | 0887624 A2 | 12/1998 | | |
| FR | 2710150 A1 | 3/1995 | | |
| GB | 2243210 A | 10/1991 | | |
| IT | WO2010/058438 | * 5/2010 | ............. | G01K 11/32 |
| WO | 2010058438 A1 | 5/2010 | | |

OTHER PUBLICATIONS

Vladimir A. Saetchnikov "Measurement of temperature and strain using Brillouin optical frequency domain analysis method", 2002.*
(Continued)

*Primary Examiner* — Michael A Lyons
*Assistant Examiner* — Maurice Smith
(74) *Attorney, Agent, or Firm* — Pearne & Gordon LLP

(57) ABSTRACT

The present invention relates to a Brillouin optoelectronic measurement method comprising the step of, providing a signal (s1) in an optical fiber (100), wherein said signal (s1) is time-frequency coded. The present invention further relates to a corresponding device for use in such a method.

18 Claims, 8 Drawing Sheets

(56) References Cited

OTHER PUBLICATIONS

Gabriele Bolognini, "Analysis of Brillouin-Based Distributed Fiber Sensors Using Optical Pulse Coding", 2008.*

Mostafa Ahangrani Farahani, "Spontaneous Raman Scattering in Optical Fibers with Modulated Probe Light for Distributed Temperature Raman Remote Sensing", Aug. 8, 1999.*

A. Wosniok, "Distributed Fibre Optic Sensor System for Temperature and Strain Monitoring Based on Brillouin Optical-Fibre Frequency-Domain Analysis", 2009.*

Marcel A. Soto "Analysis of optical pulse coding in spontaneous Brillouin-based distributed temperature sensors", Nov. 10, 2008.*

International Search Report for PCT/EP2010/070585 dated Sep. 2, 2011.

* cited by examiner

| Seq | Pos[1] | Pos[2] | Pos[3] | Pos[4] | Pos[5] |
|-----|--------|--------|--------|--------|--------|
| 1   | 1.     | 2.     | 4.     | 2.     | 0.     |
| 2   | 2.     | 3.     | 5.     | 3.     | 0.     |
| 3   | 3.     | 4.     | 1.     | 4.     | 0.     |
| 4   | 4.     | 5.     | 2.     | 5.     | 0.     |
| 5   | 5.     | 1.     | 3.     | 1.     | 0.     |
| 6   | 0.     | 1.     | 2.     | 4.     | 2.     |
| 7   | 0.     | 2.     | 3.     | 5.     | 3.     |
| 8   | 0.     | 3.     | 4.     | 1.     | 4.     |
| 9   | 0.     | 4.     | 5.     | 2.     | 5.     |
| 10  | 0.     | 5.     | 1.     | 3.     | 1.     |
| 11  | 2.     | 0.     | 1.     | 2.     | 4.     |
| 12  | 3.     | 0.     | 2.     | 3.     | 5.     |
| :   | :      | :      | :      | :      | :      |

Fig. 5

BRILLOUIN OPTOELECTRONIC MEASUREMENT METHOD AND APPARATUS

FIELD OF THE INVENTION

The present invention relates to an optoelectronic measurement method and device. In particular, but not exclusively, the present invention relates to an optoelectronic measurement method and device which can be used to monitor physical characteristics of an engineering structure.

DESCRIPTION OF RELATED ART

In many fields of application, like pipeline, power cables or subsea, the use of measuring apparatuses to monitor continuously structural and/or functional parameters is well known. The measuring apparatuses can be applied also to the civil engineering sector, and in particular in the field of the construction of structures of great dimensions.

The measuring apparatuses are commonly used to control the trend over time of the temperature or of the strain, i.e. of the geometrical measure of the deformation or elongation resulting from stresses and defining the amount of stretch or compression along the fibre, of the respective structure. In more detail, these measuring apparatuses are suitable to give information of local nature, and they can be therefore used to monitor, as a function of the time, the temperature or the strain associated with a plurality of portions and/or of components of the engineering structure to be monitored, providing useful information on leak, ground movement, deformation, etc. of the structure.

Among the measuring apparatuses used to monitor the status of engineered or architectonic structures, the optoelectronic devices based upon optical fibres have a great significance. In particular, these apparatuses normally comprise an electronic measuring device, provided with an optical fibre probe which is usually in the order of a few tens of kilometers. In use, this optical fibre is coupled stably to, and maintained substantially into contact with, portions or components of the engineered structure, whose respective physical parameters shall be monitored. For example, this optical fibre can run along the pipes of an oil pipeline, or it can be immersed in a concrete pillar of a building, so that it can be used to display the local trend of the temperature or of the strain of these structures. In other words these optoelectronic devices comprise fibre optical sensors, i.e. sensors using the optical fibre as the sensing element. Fibre optical sensors can be:

point sensors, wherein only one location along the optical fibre is made sensitive to the temperature and/or the strain;
quasi-distributed sensors or multiplexed sensors, wherein many point sensors are connected to each other by an optical fibre and multiplexed along the length of the fibre by using different wavelength of light for each sensor; or
distributed or fully distributed sensors, wherein the optical fibre is a long uninterrupted linear sensor.

These measuring instruments based upon optical fibres can be subdivided into various types depending upon both the physical quantity/ies they are suitable to measure and the physical principle used to detect this quantity/these quantities.

When a powerful light pulse of wavelength $\lambda_0$ (or frequency $v_0 = c/\lambda_0$, wherein c is the speed of light), known as the pump, propagates through an optical fibre, a small amount of the incident power is scattered in every directions due to local non-homogeneities within the optical fibre. If the optical fibre is a single-mode fibre (SMF), i.e. a fibre designed for carrying a single ray of light (mode) only, then only forward and backward scattering are relevant since the scattered light in other directions is not guided. Backscattering is of particular interest since it propagates back to the fibre end where the laser light was originally launched into the optical fibre.

Scattering processes originate from material impurities (Raleigh scattering), thermally excited acoustic waves (Brillouin scattering) or atomic or molecular vibrations (Raman scattering).

Distributing sensing techniques relay on the analysis of the backscattered signal created at different location along the fibre.

RAYLEIGH SCATTERING is the interaction of a light pulse with material impurities. It is the largest of the three backscattered signals in silica fibres and has the same wavelength as the incident light. Rayleigh scattering is the physical principle behind Optical Time Domain Reflectometer (OTDR).

BRILLOUIN SCATTERING is the interaction of a light pulse with thermally excited acoustic waves (also called acoustic phonons). Acoustic waves, through the elasto-optic effect, slightly, locally and periodically modify the index of refraction. The corresponding moving grating reflects back a small amount of the incident light and shifts its frequency (or wavelength) due to the Doppler Effect. The shift depends on the acoustic velocity in the fibre while its sign depends on the propagation direction of the travelling acoustic waves. Thus, Brillouin backscattering is created at two different frequencies around the incident light, called the Stokes and the Anti-Stokes components. In silica fibres, the Brillouin frequency shift is in the 10 GHz range (0.1 nm in the 1550 nm wavelength range) and is temperature and strain dependent.

RAMAN SCATTERING is the interaction of a light pulse with thermally excited atomic or molecular vibrations (optical phonons) and is the smallest of the three backscattered signals in intensity. Raman scattering exhibits a large frequency shift of typically 13 THz in silica fibres, corresponding to 100 nm at a wavelength of 1550 nm. The Raman Anti-Stokes component intensity is temperature dependent whereas the Stokes component is nearly temperature insensitive.

FIG. 1 schematically shows a spectrum of the backscattered light generated at every point along the optical fibre when a laser light is launched in the optical fibre. The higher peak, at the wavelength $\lambda_0$, corresponding to the wavelength of a single mode laser, is the Rayleigh peak, originated from material impurities. The so-called Stokes components and the so-called anti-Stokes components are the peaks at the right side respectively left side of the Rayleigh peak. The anti-Stokes Raman peak, originated from atomic or molecular vibrations, has an amplitude depending on the temperature T. The Stokes and anti-Stokes Brillouin peaks, generated from thermally excited acoustic waves, have a frequency depending on the temperature T and on the strain $\epsilon$.

The Brillouin shift (wavelength position with respect to the original laser light) is an intrinsic physical property of the fibre material and provides important information about the strain and temperature distribution experienced by an optical fibre.

The frequency information of Brillouin backscattered light can be exploited to measure the local temperature or strain information along an optical fibre. Standard or special single-mode telecommunication fibres and cables can be used as sensing elements. The technique of measuring the local temperature or strain is referred to as a frequency-based technique since the temperature or strain information is contained in the Brillouin frequency shift. It is inherently more reliable and more stable than any intensity-based technique, based on the Raman effect, which are sensitive to drifts, losses and variations of attenuations. As a result, the Brillouin based technique offers long term stability and large immunity to attenuation. In addition, the Brillouin scattering must satisfy a very strict phase condition, making the interaction to manifest as a spectrally narrow resonance, resulting in an accurate measurement. This process of propagating a pulse of light into the optical fibre and measuring the backscattering signal is called Spontaneous Brillouin Scattering (SPBS): it is a weak processing which leads to a low intensity scattered light.

The Brillouin scattering process has the particularity that it can be stimulated by a second optical signal—called the probe—in addition to the first optical signal—called the pump—that generated the scattering, providing that the probe fulfils specific conditions. This property is especially interesting for sensing applications and can be achieved by the use of a probe counter propagating with respect to the pump. Stimulation is maximized when pump and probe frequencies (or wavelengths) are exactly separated by the Brillouin shift. In this case, the energy transferred from the pump to the probe (or vice and versa depending on the selected Stokes/antistokes backscattering signal) results in a greatly enhanced backscattered intensity and thus a larger Signal-to-Noise Ratio (SNR). This is seen as a resonant phenomenon where an amplification of the probe power occurs at the expense of the pump when the resonant condition is fulfilled, i.e. when the frequency difference between pump and probe matches the local Brillouin frequency.

In the known solutions the pump is composed by one or more nanoseconds long optical pulses and the probe by a Continuous Wave—CW light, as it will be discussed.

Optoelectronic measurement devices based on Stimulated Brillouin Backscattering (SBS) are known as Brillouin Optical Time Domain Analysers or BOTDA; as opposed to Brillouin Optical Time Domain Reflectometers (BOTDR) which are based on spontaneous Brillouin backscattering (SPBS).

An optoelectronic measurement device based on BOTDA normally performs a frequency domain analysis and a time domain analysis.

Frequency domain analysis: the temperature/strain information is coded in the Brillouin frequency shift. Scanning the probe frequency with respect to the pump while monitoring the intensity of the backscattered signal allows to find the Brillouin gain peak, and thus the corresponding Brillouin shift, from which the temperature or the strain can be computed. This is achieved by using two optical sources, e.g. lasers, or a single optical source from which both the pump signal and the probe signal are created. In this case, an optical modulator (typically a telecommunication component) is used to scan the probe frequency in a controlled manner.

Time domain analysis: due to the pulsed nature of the pump, the pump/probe interaction takes place at different location along the fibre at different times. For any given location, the portion of probe signal which interacted with the pump arrives on a detector after a time delay equal to twice the travelling time from the fibre input to the specified location. Thus, monitoring the backscattered intensity with respect to time, while knowing the speed of light in the fibre, provides information on the position where the scattering took place.

Typical commercial optoelectronic measurement devices based on BOTDA can measure temperature/strain over 30 km of fibre with a spatial resolution of 1 m (equivalent to 30'000 distinct independent sensors). The resolution on temperature is typically <1 K. The limits are given by the fibre linear loss and the presence of other nonlinear effects screening the interaction that prohibit any power increase to compensate the loss.

However, it is important to offer an optoelectronic measurement device with a 100 km range and a metric spatial resolution. Most of the proposed solutions are not satisfactory since they require a complex remotely powered hardware that is not an attractive solution.

A smart coding using a pulse sequence can improve the signal-to-noise ratio, all other measuring characteristics being maintained (measurement time, spatial resolution and temperature accuracy). With standard fibre loss, this already corresponds to measure temperature/strain over 50 km of fibre. This demonstration was based on a coding called SIMPLEX, commonly used in other domains in engineering. The implementation of such a coding requires no modification of the hardware of the device, just a change in the software driving the device and a substantial overhead in calculations, so that it can be seen like an upgrade at a very low added cost. However, SIMPLEX code is efficient if it is composed by "return to zero" (RZ) signals, which are more difficult to manage than "non return to zero" (NRZ) signals which limits its practicality.

To improve the signal-to-noise ratio of the acquired signals it is known to intensity code the first and second electromagnetic radiation signals used in the techniques based upon SBS. However, such coding does not provide a satisfactory solution as the signal to noise ratio of the acquired signals is still not significantly increased. Accordingly, the spatial resolution and the accuracy of the performed measurements of temperature and deformation is still significantly compromised.

WO10058438A describes a measuring optoelectronics apparatus for monitoring physical characteristics of a structure based on the stimulated Brillouin scattering. In this case it comprises optical source(s) for emitting a first and a second radiation propagating in opposite directions along the fibre. The apparatus is based on time coded signals (Simplex).

GB2243210 relates to a distributed optical fibre sensor using stimulated Brillouin backscatter (SBS) for detecting temperature, strain and any external parameter which affects the frequency or the phase or the amplitude of the optical backscatter.

FR2710150 relates to a device for measuring Brillouin scattering designed to generate a pumping signal and a test signal which are injected to one end of the fiber. The value of the Brillouin scattering in the fibre allows the determination of physical parameters external to the fibre. The document describes only signal time coding.

EP0887624 relates to an optical fiber distortion measurement system (i.e., device and method) is provided to perform measurement on a measured optical fiber, which is constructed by alternatively connecting two kinds of optical fibers whose Brillouin frequency shifts are different from each other. Herein, the system sequentially supplies optical pulses to the measured optical fiber while changing their light frequencies, so that Brillouin backscattering beams are output from the measured optical fiber. At first, the system supplies an optical pulse having a prescribed light frequency to the measured optical fiber of a non-distortion state, so that the device produces initial data representing time-related variations of light intensity of Brillouin backscattering light output from the measured optical fiber. Then, the system measures a time-related variation waveform representing light intensity of Brillouin backscattering light, which is output from the measured optical fiber supplied with the optical pulse of the prescribed light frequency. By comparing the measured time-related variation waveform with the initial data, the system determines occurrence of distortion in the measured optical fiber. Thereafter, the system discriminates a kind of the distortion, which corresponds to expansion or contraction, on the basis of a relationship between Brillouin frequency shifts, which are respectively calculated with respect to a detection point and its adjacent point on the measured time-related variation waveform.

US 2010/014071 frequency-scanned optical time domain reflectometry technique includes launching a plurality of interrogating pulses into an optical fiber at a plurality of optical carrier frequencies. A Rayleigh backscatter signal is detected for each interrogating pulse as a function of time between the launching of the pulse and the detection of the backscatter signal. The time resolved Rayleigh backscatter signal at each optical frequency may then be examined to determine a distribution of a physical parameter along the length of the optical fiber.

Therefore, in view of the above description, the problem of having available an optoelectronic measuring method and apparatus, which is used to measure contemporaneously the change over time both of the local temperature and of the local strain of an engineering or architectonical structure, is currently solved in a dissatisfactory manner and represents an interesting challenge for the Applicant, which has the object of providing a measuring apparatus, which is at the same time efficient, economical and reliable.

There is a need to improve the efficiency of the optoelectronic measurements, corresponding to augmenting the range with the known spatial resolution, or, in other words, maintaining the range and augmenting spatial resolution.

It is an aim of the present invention to obviate or mitigate one or more of the aforementioned disadvantages.

BRIEF SUMMARY OF THE INVENTION

According to a first aspect of the present invention there is provided a Brillouin optoelectronic measurement method comprising the step of, providing a signal in an optical fibre, wherein said signal is time-frequency coded.

In one embodiment the signal that is time frequency coded may be constitutive of two or more wavelengths, each one being time frequency coded.

The inventive method applies to a BOTDA system as well as to a BOTDR system. In both cases the time-frequency coded signal is the pump signal. In a BOTDA system the probe signal is not time-frequency coded.

In this context a "time-frequency coded" signal means a signal comprising a sequence of code-words, each code-word comprising at least two pulses or code-letter, each pulse or code-letter of a code-word showing a different frequency.

Each code letter in fact is a pulse signal, having an amplitude, a frequency and a temporal duration. The amplitude can be zero or a fixed value, in the following normalised to 1; the frequency is different for each pulse, as will be described and the temporal duration in one preferred embodiment is in the order of nanoseconds. A code word, comprising at least two code letters, is not necessarily a "return to zero" (RZ) signal.

According to one embodiment, the inventive method further comprises the following steps Defining at least two code-words, each code-word comprising at least two code-letters, each code-letter of a code-word being associated to with different frequency Building a coding matrix S by using the defined at least two code-words Time-frequency coding a signal by using said coding matrix S Providing said signal in an optical fibre of an optical system based on a Brillouin effect (both BOTDA and BOTDR)

Measuring the optical fibre response to the signal and building the corresponding measured matrix S'.

Building an inverse matrix $S^{-1}$ of the coding matrix S

Based on said measure and on said inverse matrix, decoding said optical fibre response.

As the pump signal used in the optoelectronic measurement method is time-frequency coded, it is easier to distinguish from noise compared to non-coded or intensity coded signals; consequently a higher signal to noise ratio is achieved. As a result of the higher signal to noise ratio, improved spatial resolution is achieved and the distance over which temperature or strain conditions can be measured and monitored is increased.

Advantageously, the improved signal to noise ratio is achieved without a penalty on acquisition time and with a minimum hardware overhead.

Advantageously the method according to the invention minimizes possible drifts in temperature/strain measurements. Moreover, due to the wide range of the coded frequencies, it allows lower signal depletions, compared to monofrequency codes, e.g. Simplex code.

Moreover the longer the length L of a code-word, the higher the coding gain compared to the known solutions. Since the matrix S presents, as will be discussed, a symmetry that is a rotation of some sub-matrixes M, this symmetry allows to minimize the noise after the decoding.

According to one embodiment, the inventive method applied to a optical system which is configured to measure a Stimulated Brillouin effect (BOTDA) further comprises the following steps transmitting a first signal in a first direction along an optical fibre, wherein the first signal is a time-frequency coded signal;

transmitting a second signal in a second direction along the optical fibre, such that the first and second signals interact within the optical fibre and form a combined signal;

probing the optical fibre at one or more probe points to measure the combined signal.

According to another embodiment, the inventive method applied to a optical system which is configured to measure a spontaneous Brillouin effect (BOTDR) further comprises the following steps transmitting a first signal in a first direction along an optical fibre, wherein the first signal is a time-frequency coded signal probing the optical fibre at one or more probe points to measure a backscattered signal.

According to the inventive method, it is possible to identify irregularities in the optical fibre based on one or more characteristics of the measured combined signal. By probing the optical fibre, it is possible to measure a time coded signal component and a frequency coded signal component of a combined signal. The resonance condition is then determined based on the measured frequency coded signal component.

The invention concerns also an optoelectronic measurement device suitable for use in a Brillouin optoelectronic measurement method, the device comprising, means for time-frequency coding a signal which is to be provided in an optical fibre when carrying out in the Brillouin optoelectronic measurement method.

The device according to the invention comprises a frequency generator suitable for time-frequency coding a signal by using a coding matrix S built starting from the definition of at least two code-words, each code-word comprising at least two code-letters, each code-letter of a code-word being associated to a different frequency.

In one embodiment the frequency generator is arranged for changing the frequency at a rate equal to the duration of a code-letter, which can be in the order of nanoseconds.

Advantageously the device according to the invention allows typically a spatial resolution of 1 m with a known range (50 km) or up to typically a 100 km range with a known spatial resolution (5 m).

The spatial resolution of the method depends on temporal length of the code-letters which form the time-frequency coded signal.

BRIEF DESCRIPTION OF THE DRAWINGS

An embodiment of the invention will now be described by way of example only, with reference to the accompanying drawings in which.

FIG. 5 is an example of possible code-words of a code having a length L=5.

DETAILED DESCRIPTION OF POSSIBLE EMBODIMENTS OF THE INVENTION

Figure 1:
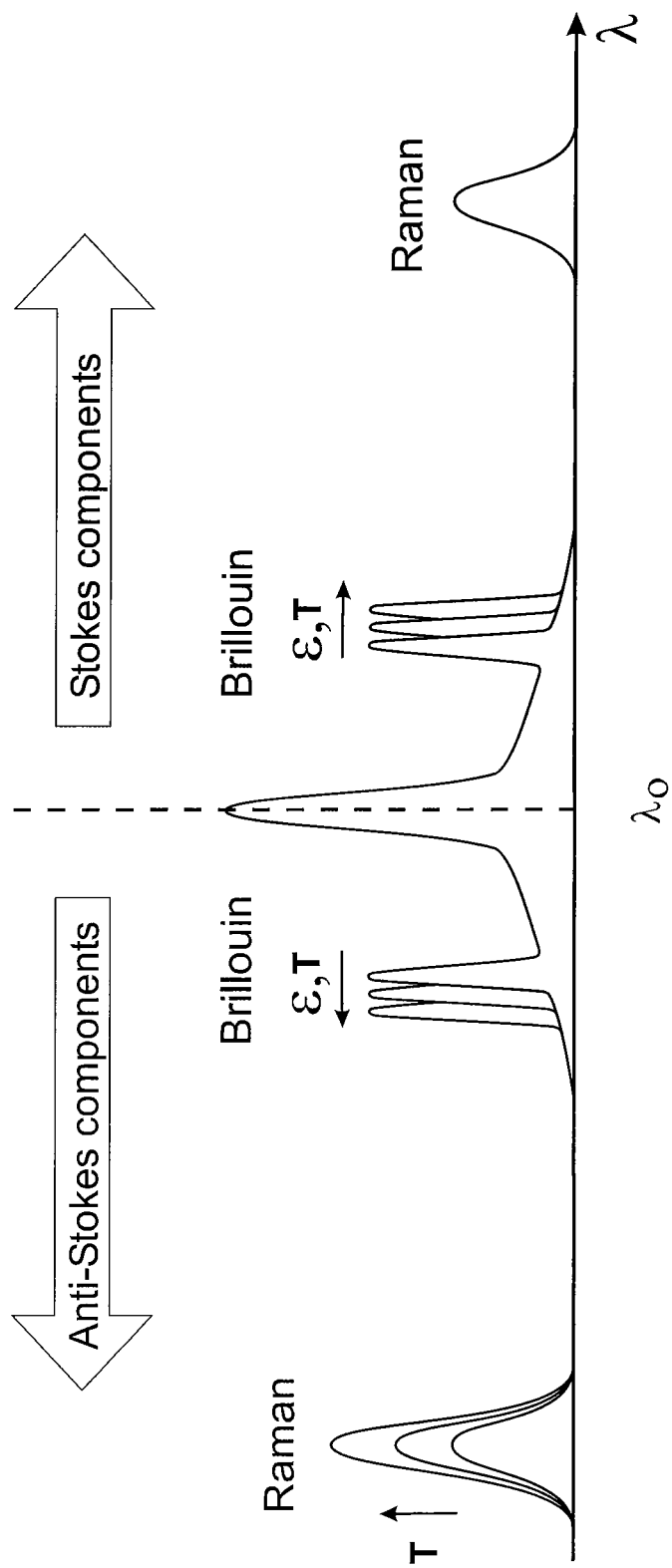
FIG. 1 shows a view of the backscattered light components of a light launched in a single-mode optical fibre.
Figure 2:
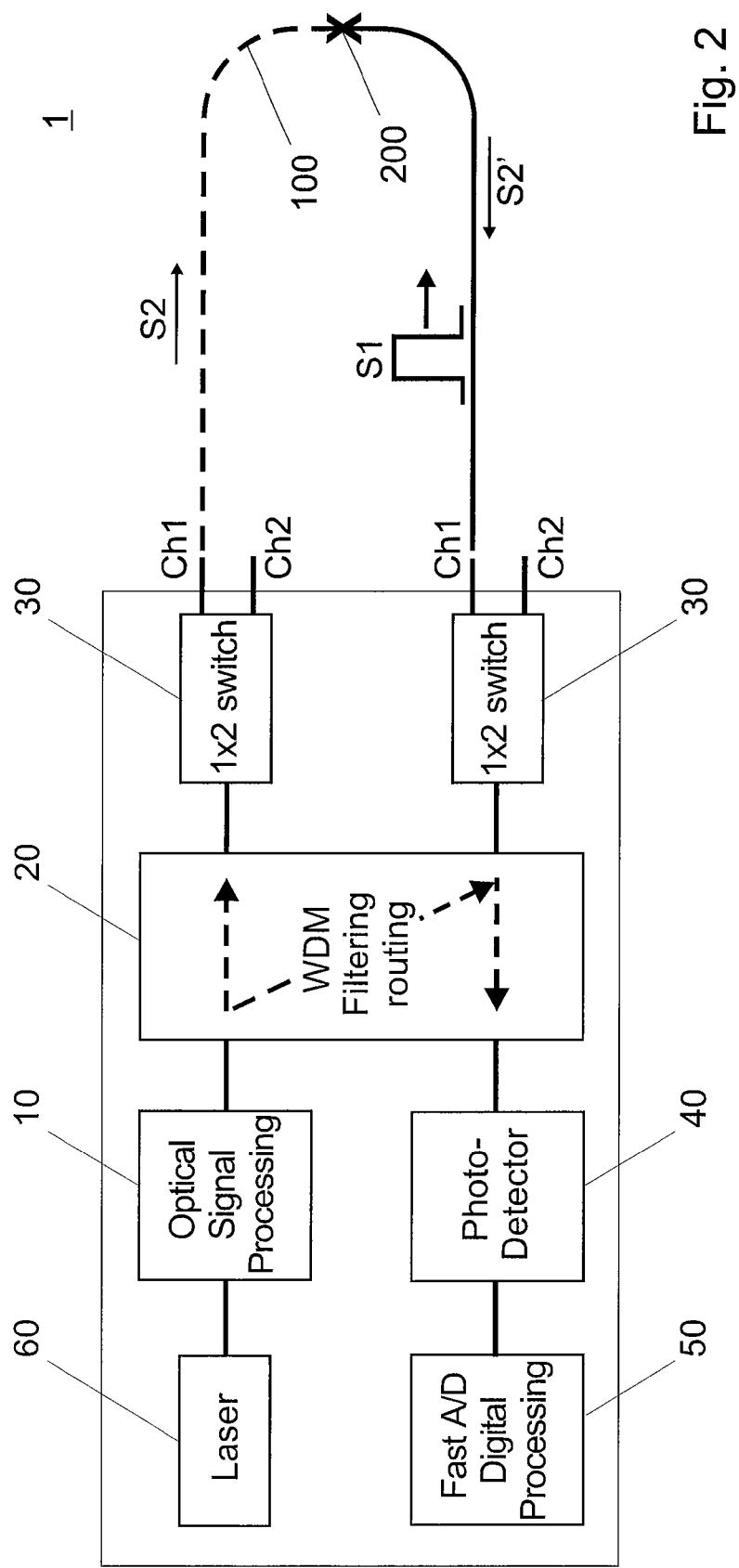
FIG. 2 is a schematic illustrating an optical fibre in which the optoelectronic measurement method, according to the present invention, is carried out using an optoelectronic measurement device according to the present invention, applied to BOTDA.

FIG. 2 is a schematic illustrating an optical fibre 100 in which the optoelectronic measurement method, according to the present invention, is carried out by using an optoelectronic measurement device 1 according to the present invention.

FIG. 2 refers to BOTDA. However the method and device according to the invention are not limited to BOTDA, but can apply also to BOTDR and in general to any optical system based on a Brillouin effect.

The device 1 comprises an optical source, e.g. a laser, operating at a determined wavelength, e.g. at 1550 nm. It is followed by an optical signal processing 10, arranged to generate the first signal s1, or pump, which is time-frequency coded and the second signal s2, or probe. In another embodiment two optical sources, e.g. two lasers, generate separately s1 and s2.

A Wavelength Division Multiplexing (WDM) filter 20 separates s1 and s2. In a preferred embodiment two 1×N switches 30 can manage N channels, where N is an integer number superior than 1, e.g. 2.

In one embodiment the optical fibre 100 comprises two fibres—a return fibre and a sensing fibre—connected to each other by a connector or a splice, each fibre being connected to a channel ch1 or ch2 of each switch 30.

A photo-detector (PD) 40 is arranged for detecting the backscattered probe signal s2' as a function of time, which is digitalized and processed by a fast A/D digital processing 50.

In one preferred embodiment the optical source is a laser DFB (Distributed FeedBack).

An optical signal processing 10 can allow to time-frequency code the first signal s1 or pump. The optoelectronic measurement device may comprise a frequency generator suitable for time-frequency coding the signal by using the coding matrix S.

In one embodiment the frequency generator could comprise a DFB laser 60 as optical source, an electro-optic modulator (EOM) 16 driven by a RF source, a mixer and a Direct Digital Synthesizer 14 (DDS); the DDS could be connected to a FPGA for handling the said code words.

The modulator 16 could be biased to operate in a suppress carrier scheme, so that the lower or upper sideband, depending on the Brillouin loss/gain configuration modulation, can be used as pump signal s1 after suppressing the upper or lower sideband by using for example a Fibre Bragg Grating (FBG). In one embodiment an amplifier, for example an Erbium Doped Fibre Amplifier (EDFA), could be used for amplifying s1.

The light from the same optical source 60 is used to synthesize the second signal s2 or probe. The device can comprise an insulator 70 for allowing to transmitting the second signal s2 in only one direction. An optical circulator 80 allows to manage the s1 and s2 directions.

The optoelectronic measurement device may comprise a measurement means suitable for measuring the optical fibre response to said signal. The measurement means could be a photo-detector (PD) 40, arranged for detecting the backscattered probe signal s2' as a function of time.

A FPGA or a DDS are examples of calculating means suitable for defining at least two code-words or sequences, each code-word comprising at least two code-letters, each code-letter of a code-word being associated to a different frequency and for building a coding matrix S by using the defined at least two code-words.

Figure 3:
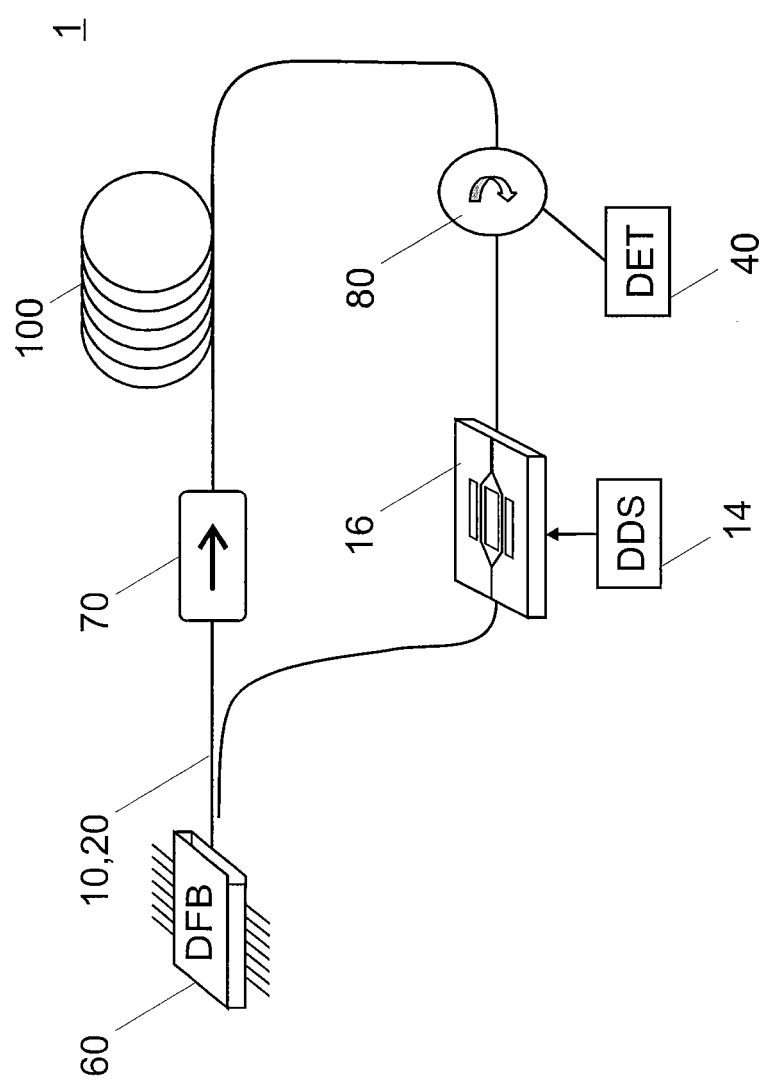
FIG. 3 is a schematic illustrating an example of an optoelectronic measurement device according to the present invention, applied to BOTDA.
Figure 4:
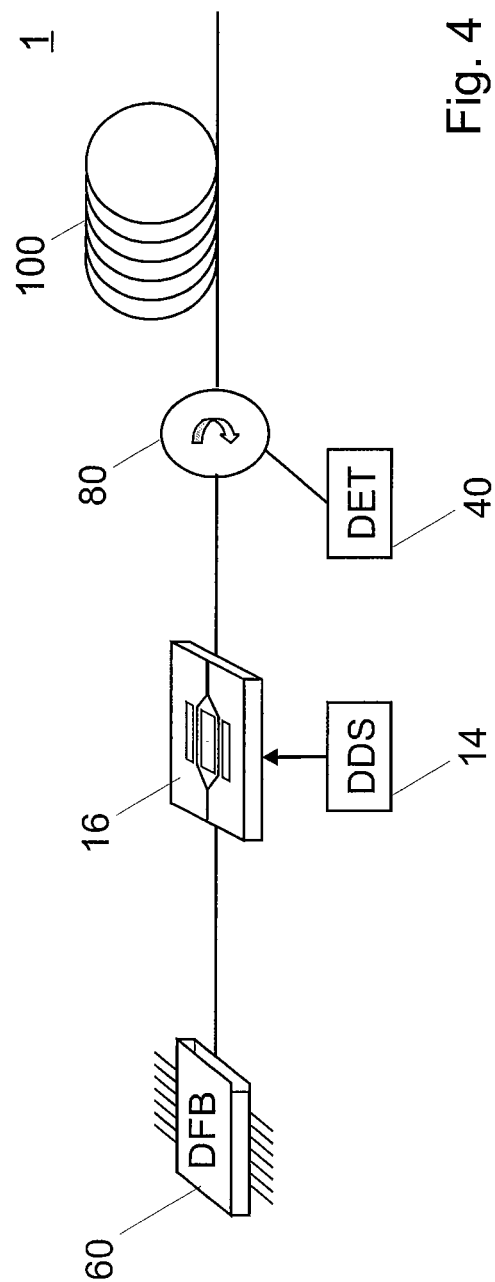
FIG. 4 is a schematic illustrating an example of an optoelectronic measurement device according to the present invention, applied to a BOTDR.

FIG. 3 shows a simplified example of a BOTDA system according to the invention. The invention can also be applied to a BOTDR system, illustrated in FIG. 4. According to this embodiment of the invention, the measurement device includes a optical source 60, an electro-optic modulator (EOM) 16 driven by a RF source, a mixer and a Direct Digital Synthesizer 14 (DDS) arranged to launch a time-frequency coded signal (s1) into the fibre 100, as explained above. The optical circulator 80 and the photo-detector 40 are arranged to measure a backscattered signal generated by spontaneous Brillouin backscatter in the fibre 100.

The length "L" of the time-frequency code-word, i.e. the number of its code-letters, is equal to the number of frequencies which can be used for time-frequency coding signal. In one preferred embodiment L is a prime number. In another embodiment, one of these frequencies may appear at most two times in a code-word.

In one preferred embodiment each code-word contains at least one code-letter associated to a frequency equal to a zero of the matrix S, corresponding to a frequency where the Brillouin gain is zero: in other words the number of code-letters associated to frequencies different to a zero of the Matrix S used in each code-word is equal to L−1. The presence of this zero is very useful for inversing the matrix S and then calculating $S^1$.

Each code letter is a pulse signal, having an amplitude, a frequency and a temporal duration. The amplitude can be zero or a fixed value, in the following normalised to 1; the frequency is different for each pulse and the temporal duration in one preferred embodiment is in the order of nanoseconds. A code word, comprising at least two code letters, is not necessarily a "return to zero" (RZ) signal. A "non return to zero" (NRZ) signal is less difficult to manage than a RZ signal.

FIG. 5 is an example of possible code-words or sequences of a code having a length L=5. The expressions "Pos[1], Pos[2], . . . , Pos[5]" indicate the temporal position of the code-letters or pulses forming a code-word, for giving a temporal order. In particular Pos[5] temporally follows the Pos [4], which temporally follows the Pos[3] and so on.

Figure 6:
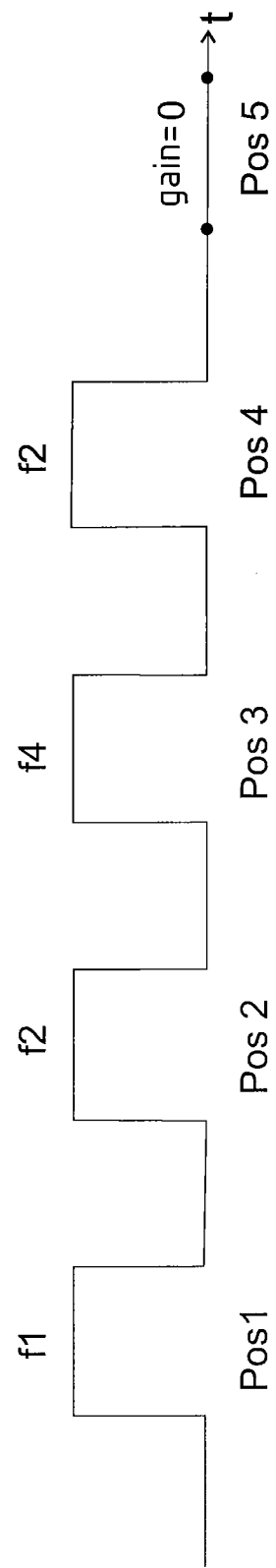
FIG. 6 is an example of the first code-word of FIG. 5.

If one takes the first line of the table of FIG. 5, one obtains a first code-word, illustrated on FIG. 6, which is composed by five code-letters:
- at Pos[1] there is a first code-letter corresponding to a frequency f1
- at Pos[2] there is a second code-letter corresponding to a frequency f2
- at Pos[3] there is a third code-letter corresponding to a frequency f4
- at Pos[4] there is a fourth code-letter corresponding to a frequency f2
- at Pos[5] there is a fifth code-letter corresponding to a frequency where the Brillouin gain is 0.

The length "L", in this case L=5, of the time-frequency code-word, i.e. the number of its code-letters, is equal to the number of frequencies (f1 to f5) which can be used for time-frequency coding signal. In this case one of these frequencies may appear at most two times in a code-word. For example in the code-word of FIG. 6 the frequency f2 appears two times, at Pos[2] and Pos[4].

Each code-word contains at least one code-letter associated to a frequency corresponding to a zero Brillouin gain. The presence of this zero is used for inversing the matrix S and then calculating $S^{-1}$.

The code-words at the lines 2 to 5 on FIG. 5 are obtained by vertically rotating the frequencies of each temporal position Pos[1] to Pos[4], in such a manner that each code-word 2 to 5 comprises at most two code-letters having the same frequency. Referring for example to the Pos[1], column C1, the first code-word has in this position the frequency f1, the second code-word f2, the third code-word f3, the fourth f4 and the fifth f5.

The following code-words 6 to 10 are obtained from the code-words 1 to 5 by rotating the column C1 and the following columns as indicated in FIG. 5. The same apply to code-words 11 to 15 and so on.

Figure 7:
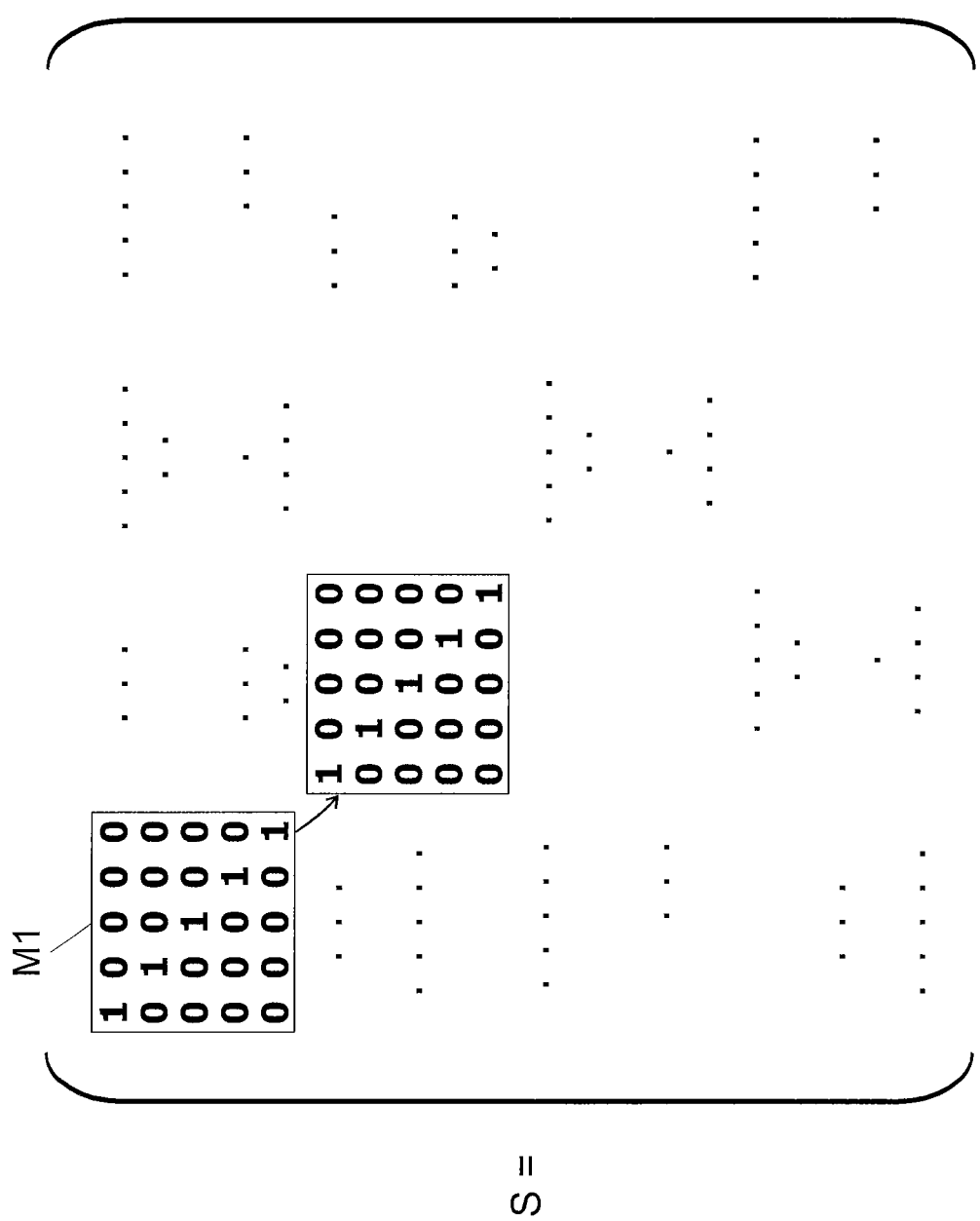
FIG. 7 is an example of coding matrix S built starting from the code-words of FIG. 5.

FIG. 7 is an example of coding matrix S built starting from the code-words of FIG. 5.

Advantageously the coding matrix S contains L×L different sub-matrixes M, i.e. L sub-matrixes M, each sub-matrix M being placed L times in the matrix S according to a rotation criterion.

Each sub-matrix M is of dimensions L×L. The first row of the first sub-matrix M is a representation of the first code-letter of the first code-word. In the example illustrated in FIG. 7, the first line of the first sub-matrix M1 is [1, 0, 0, 0, 0], indicating that in the position Pos[1] the frequency of the code-letter is the first frequency f1. The first line of the second sub-matrix M2, not illustrated, is [0, 1, 0, 0, 0], indicating that in the position Pos[2] the frequency of the code-letter is the second frequency f2. The first line of the third sub-matrix M3, not illustrated, is [0, 0, 0, 1, 0], indicating that in the position Pos[3] the frequency of the code-letter is the fourth frequency f4, and so on.

The first line of the matrix S is then a matrix representation of the code-word illustrated in FIG. 6.

The matrix S is obtained from different rotations of the sub-matrixes L as illustrated in FIG. 7.

The longer the code-word L, the bigger the matrix S. Moreover the longer L, the higher the coding gain compared to the known solutions, and, since the matrix S presents a symmetry that is a rotation of sub-matrixes M, this symmetry allows to minimize the noise after the decoding.

The optoelectronic measurement device may comprise a decoder, not illustrated, suitable for decoding the optical fibre response based on the measure and on the inverse matrix $S^{-1}$.

Figure 8:
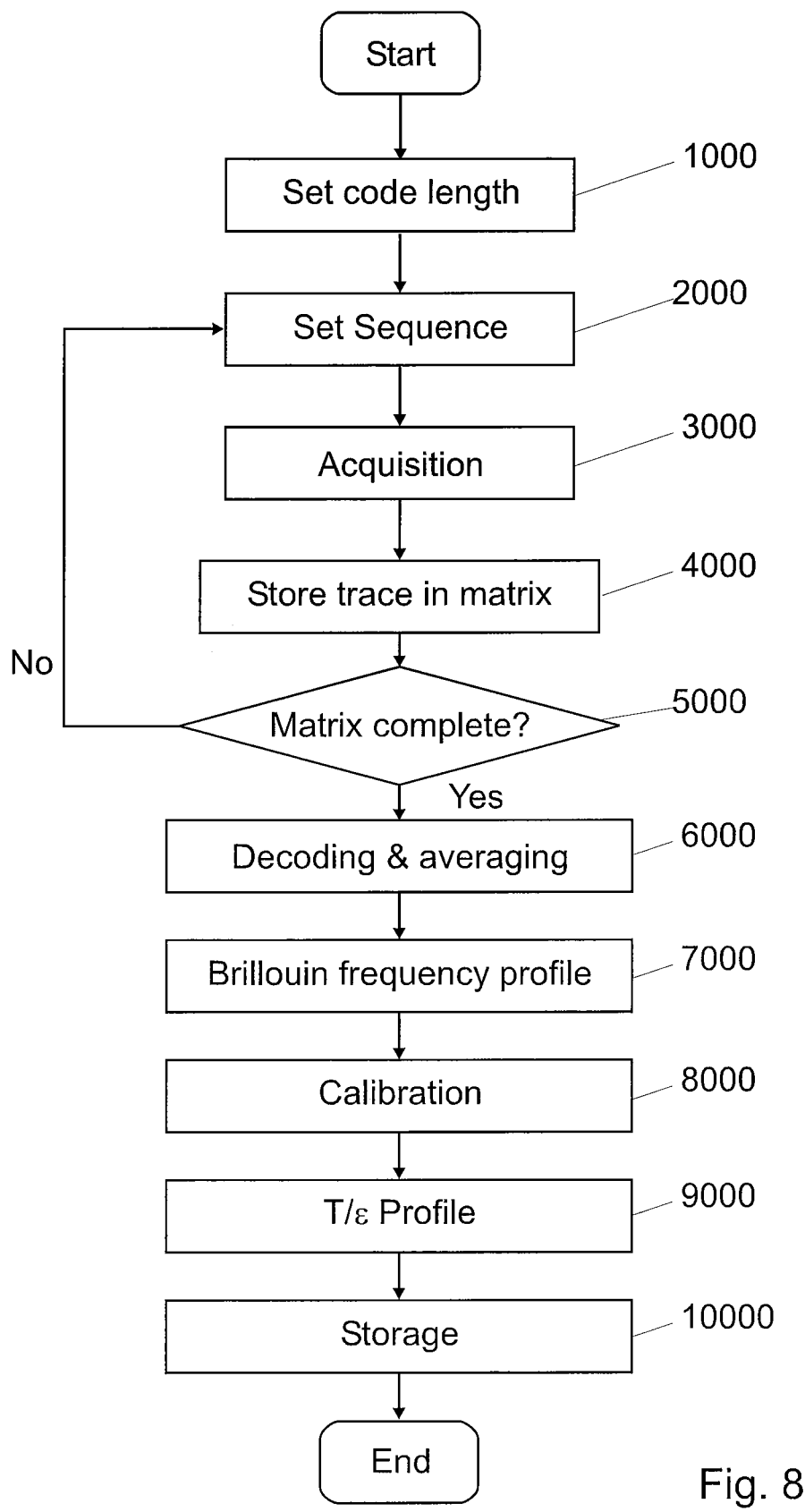
FIG. 8 is a flow chart illustrating the steps involved when using an optoelectronic measurement device according to the present invention, to detect temperature and strain variations of an optical fibre.

FIG. 8 is a flow chart illustrating the steps involved when using an optoelectronic measurement device according to the present invention, to detect temperature and strain of an optical fibre.

After the start, the code length L is set (step 1000). Then the different sequences or code-words are set (step 2000). Then the optical fibre response, in the time domain, is acquired for all the length of the optical fibre (step 3000). The acquisition corresponds to record the probe intensity as a function of time, converts the information in distance information (Distance processing and mapping), and compute the Brillouin Gain at every position along the fibre. The fibre response is constructed by performing repeated acquisition of the back-scattered signal in order to build the matrix S' expressing the measured fibre response, (step 4000). Steps 2000 to 4000 are repeated until the matrix is completed (step 5000). Then the matrix is decoded by using the inverse matrix $S^1$ (step 6000). If a point of the fibre is measured more than one time, the decoding comprises the averaging of these measurements. The Brillouin Frequency Profile, i.e. the computation of the Brillouin Frequency Shift at every position along the fibre is then computed (step 7000). At step 8000 the Brillouin Frequency Profile is converted into a strain or temperature profile (step 9000) by using fibre calibration temperature or strain data coefficients. Finally the temperature or strain profiles are stored and available for further monitoring processing (step 10000).

The code optimisation relates to the search of combinations of rotations of the sub-matrices M that minimize the variance (standard deviation). In one preferred embodiment the code has a gain equal to $(L/2)^{(1/2)}$.

Various modifications and variations to the described embodiments of the invention will be apparent to those skilled in the art without departing from the scope of the invention as defined in the appended claims. Although the invention has been described in connection with specific preferred embodiments, it should be understood that the invention as claimed should not be unduly limited to such specific embodiment.

The invention claimed is:

1. A Brillouin optoelectronic measurement method comprising steps of:
    defining a signal (s1), wherein said signal (s1) is time-frequency coded so that the signal comprises at least two code-words, and each code-word comprises at least two pulses or code-letters, and each pulse or code-letter of a code-word is associated with a different frequency;
    providing said signal in an optical fibre;
    measuring the optical fibre response to said signal; and
    monitoring physical characteristics of an engineering structure based in part on the provided signal.

2. The Brillouin optoelectronic measurement method according to claim 1, further comprising steps of:
- defining the at least two code-words, each code-word comprising at least two code-letters;
- building a coding matrix (S) using the defined at least two code-words;
- time-frequency coding said signal by using said coding matrix (S);
- building an inverse matrix ($S^{-1}$) of the coding matrix (S); and
- based on said measuring and on said inverse matrix, decoding said optical fibre response.

3. The Brillouin optoelectronic measurement method according to claim 2, wherein the coding matrix is a symmetry that is a rotation of sub-matrixes.

4. The Brillouin optoelectronic measurement method according to claim 2, wherein the measured fibre response is expressed as a matrix constructed by performing repeated acquisition of backscattered signal.

5. The Brillouin optoelectronic measurement method according to claim 1, further comprising a step of time-frequency coding each one of said two or more wavelengths when said signal (s1) comprises two or more wavelengths.

6. The Brillouin optoelectronic measurement method according to claim 1, wherein said optical system is configured to measure a stimulated Brillouin effect, the method further comprising steps of:
- transmitting a first signal (s1) in a first direction along the optical fibre, wherein the first signal (s1) is a time-frequency coded signal;
- transmitting a second signal (s2) in a second direction along the optical fibre, such that the first and second signals interact within the optical fibre and form a combined signal; and
- probing the optical fibre at one or more probe points to measure the combined signal.

7. The Brillouin optoelectronic measurement method according to claim 1, wherein said optical system is configured to measure a spontaneous Brillouin backscattering effect, the method further comprising steps of,
- transmitting a first signal (s1) in a first direction along the optical fibre, wherein the first signal (s1) is a time-frequency coded signal; and
- probing the optical fibre (100) at one or more probe points to measure a backscattered signal.

8. The method according to claim 1, further comprising a step of identifying irregularities in the optical fibre based on one or more characteristics of a measured combined signal.

9. An optoelectronic measurement device suitable for use in a Brillouin optoelectronic measurement method, the device comprising:
- calculating means configured to define at least two code-words, each code-word comprising at least two code-letters, and each pulse or code-letter of a code-word is associated with a different frequency;
- a transmitter configured to provide said signal in an optical fibre when carrying out the Brillouin optoelectronic measurement method; and
- measurement means configured to measure the optical fibre response to said signal.

10. The optoelectronic measurement device according to claim 9, further comprising:
- calculating means suitable for defining the at least two code-words, each code-word comprising at least two code-letters, for building a coding matrix (S) by using the defined at least two code-words and for calculating the inverse matrix ($S^{-1}$) of the coding matrix (S);
- a frequency generator suitable for time-frequency coding said signal by using said coding matrix (S);
- a decoder suitable for decoding said optical fibre response based on said measuring and on a inverse matrix ($S^{-1}$) of the coding matrix (S);
- wherein the calculating means builds the inverse matrix ($S^{-1}$).

11. The optoelectronic measurement device according to claim 10, wherein, said frequency generator is configured for time-frequency coding each one of said two or more wavelengths of a signal which comprises two or more wavelengths.

12. The optoelectronic measurement device according to claim 10, wherein said frequency generator is arranged for changing the frequency at a rate equal to the duration of a code-letter.

13. The optoelectronic measurement device according to claim 12, wherein said duration is in the order of nanoseconds.

14. The optoelectronic measurement device according to claim 9, wherein said optical system is suitable for use in a stimulated Brillouin optoelectronic measurement method, the device further comprising:
- a transmitter suitable for transmitting a first signal (s1) in a first direction along the optical fibre, wherein the first signal is a time-frequency coded signal;
- a transmitter suitable for transmitting a second signal (s2) in a second direction along the optical fibre, such that the first and second signals interact within the optical fibre and form a combined signal; and
- means suitable for probing the optical fibre at one or more probe points to measure the combined signal.

15. The optoelectronic measurement device according to claim 9, wherein said optical system is suitable for use in a spontaneous Brillouin optoelectronic measurement method, the device further comprising:
- a transmitter suitable for transmitting a first signal (s1) in a first direction along the optical fibre, wherein the first signal is a time-frequency coded signal;
- a detector suitable for probing the optical fibre at one or more probe points to measure a backscattered signal.

16. The optoelectronic measurement device according to claim 9, comprising:
- a light source;
- an electro-optic modulatory;
- a Direct Digital Synthesizer;
- an optical fibre;
- a circulator; and
- a photo-detector.

17. The optoelectronic measurement device according to claim 16, further comprising:
- an optical signal processing;
- an optical filtering routing;
- an insulator.

18. The optoelectronic measurement device according to claim 16, further comprising at least one selected from the group comprising Fibre Bragg grating, A/D digital processing device, mixer.

* * * * *

UNITED STATES PATENT AND TRADEMARK OFFICE
CERTIFICATE OF CORRECTION

| | | |
|---|---|---|
| PATENT NO. | : 9,116,119 B2 | Page 1 of 1 |
| APPLICATION NO. | : 13/991249 | |
| DATED | : August 25, 2015 | |
| INVENTOR(S) | : Sebastien Le Floch | |

It is certified that error appears in the above-identified patent and that said Letters Patent is hereby corrected as shown below:

In the claims,
Column 12, claim 14, line 48, please replace "modulatory" with -- modulator --

Signed and Sealed this
Twenty-second Day of March, 2016

Michelle K. Lee
*Director of the United States Patent and Trademark Office*